(12) United States Patent
Brouillette et al.

(10) Patent No.: US 11,179,169 B2
(45) Date of Patent: Nov. 23, 2021

(54) DEVICE FOR DELIVERING MECHANICAL WAVES THROUGH A BALLOON CATHETER

(71) Applicant: Les Solutions Medicales Soundbite Inc., Saint-Laurent (CA)

(72) Inventors: Martin Brouillette, Sherbrooke (CA); Louis-Philippe Riel, Montreal (CA); Steven Dion, Sherbrooke (CA); Francis Bellido, Beaconsfield (CA); Philippe Lacasse, Sherbrooke (CA); Marwan Abboud, Pierrefonds (CA); Domenic Santoianni, Kirkland (CA)

(73) Assignee: Les Solutions Medicales Soundbite Inc., Saint-Laurent (CA)

( * ) Notice: Subject to any disclaimer, the term of this patent is extended or adjusted under 35 U.S.C. 154(b) by 197 days.

(21) Appl. No.: 16/346,938

(22) PCT Filed: Nov. 3, 2017

(86) PCT No.: PCT/IB2017/056898
§ 371 (c)(1),
(2) Date: May 2, 2019

(87) PCT Pub. No.: WO2018/083666
PCT Pub. Date: May 11, 2018

(65) Prior Publication Data
US 2020/0054352 A1   Feb. 20, 2020

Related U.S. Application Data

(60) Provisional application No. 62/417,646, filed on Nov. 4, 2016.

(51) Int. Cl.
*A61B 17/22*  (2006.01)
*A61M 25/10*  (2013.01)

(52) U.S. Cl.
CPC ............ *A61B 17/22012* (2013.01); *A61B 2017/22015* (2013.01); *A61B 2017/22024* (2013.01);
(Continued)

(58) Field of Classification Search
CPC .... A61B 17/22012; A61B 2017/22015; A61B 2017/2224; A61B 2017/22025;
(Continued)

(56) References Cited

U.S. PATENT DOCUMENTS

| 5,609,606 A | 3/1997 | O'Boyle |
| 5,722,979 A * | 3/1998 | Kusleika ......... A61B 17/22012 604/22 |

(Continued)

FOREIGN PATENT DOCUMENTS

CA   2227838 A1   10/1998

OTHER PUBLICATIONS

International Search Report; Canadian Intellectual Property Office; International Application No. PCT/IB2017/056898; dated Mar. 2, 2018; 2 pages.
(Continued)

*Primary Examiner* — Julian W Woo
(74) *Attorney, Agent, or Firm* — Taft Stettinius & Hollister LLP

(57) ABSTRACT

A device for delivering mechanical waves to treat a lesion present in a blood vessel, including a catheter extending between a first proximal end and a first distal end, an inflatable balloon secured to the catheter and being adjustable between an inflated configuration and a deflated configuration, and at least one mechanical waveguide extending between a second proximal end and a second distal end for propagating at least one mechanical wave from the second proximal end to the second distal, with the mechanical (Continued)

waveguide being secured to the inflatable balloon or the catheter.

23 Claims, 10 Drawing Sheets

(52) U.S. Cl.
CPC ............... *A61B 2017/22025* (2013.01); *A61B 2017/22061* (2013.01); *A61B 2017/22062* (2013.01); *A61M 2025/105* (2013.01)

(58) Field of Classification Search
CPC .. A61B 2017/22061; A61B 2017/2206; A61B 2017/22014; A61M 2025/105
See application file for complete search history.

(56) References Cited

U.S. PATENT DOCUMENTS

| | | | |
|---|---|---|---|
| 6,083,232 A | 7/2000 | Cox | |
| 6,263,236 B1 * | 7/2001 | Kasinkas | A61B 18/24 604/21 |
| 6,464,660 B2 * | 10/2002 | Brisken | A61B 17/22012 604/22 |
| 6,979,293 B2 * | 12/2005 | Hansmann | A61B 17/22012 600/439 |
| 7,153,315 B2 | 12/2006 | Miller | |
| 9,011,430 B2 * | 4/2015 | Habib | A61B 17/22 606/41 |
| 10,245,051 B2 * | 4/2019 | Spano | A61B 17/22012 |
| 11,065,645 B2 * | 7/2021 | Brouillette | G10K 15/043 |
| 2014/0039358 A1 | 2/2014 | Zhou et al. | |
| 2014/0277002 A1 | 9/2014 | Grace | |
| 2015/0127034 A1 | 5/2015 | Eaton | |
| 2015/0343191 A1 | 12/2015 | Spano | |

OTHER PUBLICATIONS

Written Opinion of the International Searching Authority (Corrected Version); Canadian Intellectual Property Office; International Application No. PCT/IB2017/056898; dated Mar. 2, 2018; 5 pages.

* cited by examiner

DEVICE FOR DELIVERING MECHANICAL WAVES THROUGH A BALLOON CATHETER

CROSS REFERENCE TO RELATED APPLICATIONS

This application is a U.S. National Phase of International PCT Application No. PCT/IB2017/056898 filed Nov. 3, 2017, which claims the benefit of U.S. Provisional Patent Application Ser. No. 62/417,646 filed Nov. 4, 2016, the contents of each application are incorporated herein by reference in their entirety.

TECHNICAL FIELD

The present invention relates to the field of medical devices and methods, and specifically those using mechanical waves, such as ultrasound and shock waves, to perform medical treatment on cells, tissues and organs, and more particularly to treat lesions that have been hardened by the presence of calcification.

BACKGROUND

Non-invasive therapies using ultrasound or shock waves are commonly used to treat a variety of medical conditions, such as kidney stones and prostate cancer, for example. They are attractive because the source of mechanical waves is outside the body of the patient to be treated, so the procedure is not invasive. By the design of the mechanical energy source, this energy is usually focused on a target to be treated within the body. However, there are limitations to this technique. For one, the exact location of the target may be difficult to obtain due to limitations of the imaging method used. Also, the energy may not be focused at the exact desired location due to physical limitations of the focusing wave itself and heterogeneities within the various tissues and organs through which the wave travels. Finally, the energy density at the target may not be sufficient to accomplish the desired treatment.

Some balloon devices incorporate a built-in shock wave generator, but this requires bringing high-voltage high-current electricity within the patient's body, with important safety challenges. Some other balloon devices incorporate a source of ultrasound energy, but the available power levels may not be sufficient for many applications, especially those that require fracturing and/or eroding calcified tissue structures.

Therefore there is a need for an improved method and device for delivering mechanical waves.

SUMMARY

According to a first broad aspect, there is provided a device for delivering mechanical waves to treat a lesion present in a blood vessel, comprising: a catheter body extending between a first proximal end and a first distal end along a longitudinal axis; an inflatable balloon secured to the catheter body and being adjustable between an inflated configuration and a deflated configuration, the inflatable balloon; being fluidly connectable to s source of fluid for varying a configuration of the balloon; and at least one mechanical waveguide extending between a second proximal end operatively connectable to a source of mechanical waves and a second distal end for propagating the mechanical waves from the second proximal end to the second distal, the mechanical waveguide being secured to one of the inflatable balloon and the catheter.

In one embodiment, the inflatable balloon is adjacent to the first distal end of the catheter.

In one embodiment, the inflatable balloon is secured around at least a portion of the catheter device.

In one embodiment, the at least one mechanical waveguide is secured to an external face of the inflatable balloon.

In one embodiment, the second distal end of the at least one mechanical waveguide is coplanar with the first distal end of the catheter body when the inflatable balloon is inflated.

In another embodiment, the second distal end of the at least one mechanical waveguide projects from the first distal end of the catheter body when the inflatable balloon is inflated.

In a further embodiment, the second distal end of the at least one mechanical waveguide is located between the proximal and distal ends of the catheter body when the inflatable balloon is inflated.

In one embodiment, the at least one mechanical waveguide is movably secured to the external face of the inflatable balloon.

In one embodiment, the device further comprises at least one deflector each secured to the external face of the inflatable balloon and facing the second distal end of a respective one of the at least one mechanical waveguide.

In one embodiment, the deflector is adapted to deflect the mechanical waves radially.

In one embodiment, at least a section of the at least one mechanical waveguide is inserted inside the inflatable balloon.

In one embodiment, the balloon comprises an internal wall facing the catheter body and an external wall comprising at least one aperture on a distal face thereof, the at least one mechanical waveguide extending at least partially between the internal and external walls each through a respective one of the at least one aperture.

In one embodiment, the internal wall has a substantially circular cross-section shape and the external wall defines at least one protrusion each receiving a respective one of the at least one mechanical waveguide.

In another embodiment, the external wall has a substantially circular cross-section shape and the internal wall defines at least one recess each receiving a respective one of the at least one mechanical waveguide.

In one embodiment, the second distal end of the at least one mechanical waveguide is located outside of the inflatable balloon.

In one embodiment, the catheter body comprises an internal wall and an external wall spaced apart from the internal wall, the at least one mechanical waveguide being inserted between the internal and external walls, the external wall comprising at least one aperture and the at least one mechanical waveguide being inserted into a respective one of the at least one aperture so as to partially extend within the inflatable balloon.

In one embodiment, the at least one mechanical waveguide is sealingly inserted into the respective one of the at least one aperture.

In one embodiment, the second distal end of the at least one mechanical waveguide is positioned within the inflatable balloon.

In one embodiment, the second distal end of the at least one mechanical waveguide abuts against an internal face of the inflatable balloon.

In one embodiment, the device further comprises at least one deflector each secured to an internal face of the inflatable balloon and facing the second distal end of a respective one of the at least one mechanical waveguide.

In one embodiment, the deflector is adapted to deflect the mechanical waves radially.

In one embodiment, the inflatable balloon comprises at least one hole and the second distal end of the at least one mechanical waveguide is sealingly inserted into a respective one of the at least one hole.

In one embodiment, the second distal end of the at least one mechanical waveguide projects outside of the inflatable balloon.

In one embodiment, the second distal end of the at least one mechanical waveguide is straight.

In another embodiment, the second distal end of the at least one mechanical waveguide is outwardly curved.

In one embodiment, the at least one mechanical waveguide comprises a plurality of mechanical waveguides.

In one embodiment, the mechanical waveguides are arranged according to desired energy deposition pattern when the inflatable balloon is in the inflated configuration.

In one embodiment, the mechanical waveguides are evenly distributed around the inflatable balloon.

In one embodiment, the mechanical waveguides are arranged according to at least two rows when the inflatable balloon is in the deflated configuration and according a single row when the inflatable balloon is in the inflated configuration.

In one embodiment, at least a section of the at least one mechanical waveguide is covered with a sheath.

In one embodiment, the device further comprises at least one waveguide tube in which a respective one of the at least one mechanical waveguide is inserted.

In one embodiment, an external face of the inflatable balloon is coated with one of: a drug, a hydrophilic coating, a hydrophobic coating and a friction reducing coating.

In one embodiment, the sheath is coated with a drug.

In one embodiment, the at least one mechanical waveguide is adapted to propagate high amplitude and short duration mechanical pulses.

For the purpose of the present description, a mechanical wave should be understood as a signal having arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of $1/fc$.

In one embodiment, the mechanical pulse has a center frequency fc comprised between about 20 kHz and about 10 MHz. In one embodiment, the amplitude of the mechanical pulse when reaching the distal end of the catheter device is comprised between about 10 MPa and about 1000 MPa. In one embodiment, the duration of the mechanical pulse when reaching the distal end of the catheter device is in the order of $1/fc$.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
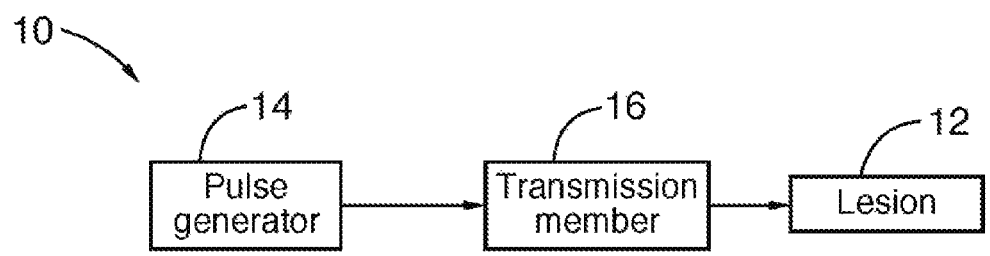
FIG. 1 is a block diagram illustrating a system for treating a lesion, in accordance with an embodiment.

FIG. 1 illustrates one embodiment of a system 10 for treating a lesion 12 to order to describe a particular context in which the present catheter is to be used. The system 10 comprises a pulse generator 14 and a transmission member 16 adapted to propagate mechanical waves or pulses.

FIG. 1 illustrates one embodiment of a system 10 for treating a lesion 12 to order to describe a particular context in which the present catheter is to be used. The system 10 comprises a pulse generator 14 and a transmission member 16 adapted to propagate mechanical waves or pulses.

The pulse generator 14 is adapted to generate a high amplitude and short duration mechanical pulse. The pulse generator 54 may comprise at least one broadband source and/or at least one narrow band source. The narrow or broad band source may be an electromechanical transducer. The pulse generator 14 may comprise a spatial concentrator to focus the output of at least one source toward a focal zone at which the proximal end of the transmission member 16 is located so as to couple the generated pulse therein.

In one embodiment, a high amplitude and short duration mechanical pulse is a mechanical pulse having a time duration of less than about 10 microseconds and an amplitude equal to or greater than about 10 bars.

The transmission member 16 such as a mechanical waveguide extends between a first or proximal end that is operatively connected to the pulse generator 14 and a second or distal end. The transmission member 16 is adapted to receive mechanical pulses at its proximal end and propagate the mechanical pulses up to its distal end. When it reaches the distal end, the mechanical pulse is at least partially transmitted to generate a transmitted pulse that propagates outside of the transmission member 16. It should be understood that a pulse may also be reflected by the distal end and propagates back in the transmission member 16 towards the proximal end thereof. The transmitted mechanical pulse corresponds to a mechanical pulse that propagates in the medium surrounding the distal end of the transmission member 16 up to the lesion 12. The transmitted pulse further propagates into the lesion 12, which may create cracks within the lesion 12, and eventually cleaves or breaks the lesion 12 into pieces.

In an embodiment in which the distal end of the transmission member 16 abuts against the lesion 12, the mechanical waveguide 16 may further be used to break the lesion 12 and/or drill a hole into the lesion 12. The transmission of the mechanical pulse at the distal end of the transmission member 16 creates a movement of the distal end of the transmission member 16. This movement may be along the longitudinal axis of the transmission member 16. Alternatively, the movement may be perpendicular to the longitudinal axis or it may be a combination of movements both along the longitudinal axis and perpendicular to the longitudinal axis of the transmission member. During this movement, the distal end of the transmission member 16 nominally first moves towards the lesion 12 and then moves back into its initial position. It should be understood that the movement may be inverted (i.e., the distal end may first move away from the lesion 12 and then towards the lesion 12) depending on the polarity of the mechanical pulse reaching the distal end of the transmission member 16. When a plurality of distinct mechanical pulses are successively transmitted at the distal end of the transmission member 16, the movement of the distal end may be seen as a jack-hammer movement which may be used to treat the lesion 12.

Figure 2:
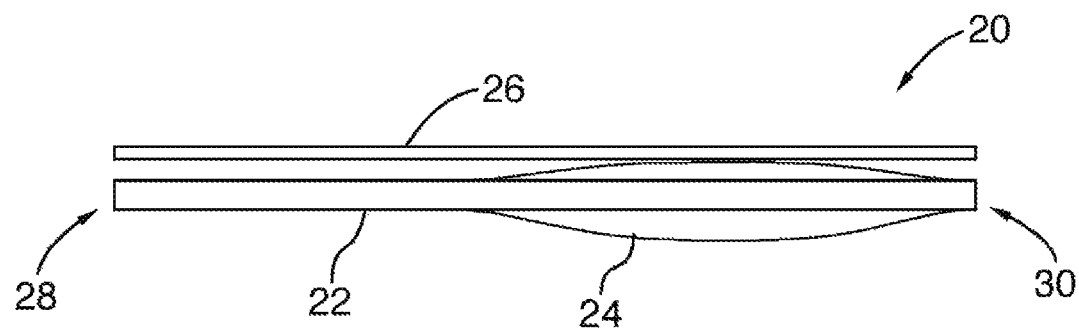
FIG. 2 is a cross-sectional view of a balloon catheter comprising a single mechanical waveguide and a balloon in a deflated state, in accordance with an embodiment.

FIG. 2 illustrates one embodiment of a balloon catheter 20 which may be used as a transmission member such as the transmission member 16 of FIG. 1 for propagating mechanical waves or pulses coming from an extracorporeal mechanical energy source such as a source of short duration shock waves or ultrasound pulses.

The balloon catheter 20 comprises a catheter shaft or elongated and hollow body 22 centrally positioned, a balloon 24 mounted on the catheter shaft 22 and a mechanical waveguide 26 mounted on the external face of the balloon 24. The catheter shaft 22 extends between a proximal end 28 and a distal end 30 which is adapted to be inserted into a blood vessel of a patient such as an artery. The catheter shaft 22 is hollow so as to allow a guide wire to extend therethrough from its proximal end 28 to its distal end 30.

The balloon 24 is secured to the catheter shaft 22 adjacent the distal end 30 thereof. The balloon 24 is hermetically secured around the external face of the catheter shaft 22 so as to surround the catheter shaft 22. In FIG. 2, the balloon 24 is shown in a deflated state/configuration.

The mechanical waveguide 26 is adapted to propagate a mechanical wave, such as a shock wave or an ultrasound pulse, which is generated by a source of mechanical waves (not shown) positioned outside of the patient. The proximal end of the mechanical waveguide 26 is operatively connected to the source of mechanical waves so that the mechanical waves propagate along the mechanical waveguide 26 up to its distal end.

Figure 3:
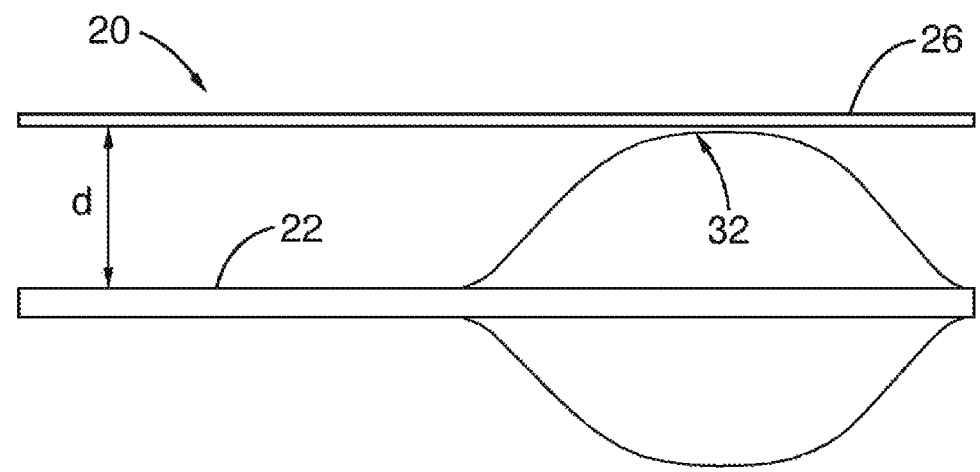
FIG. 3 is a cross-sectional view of a balloon catheter of FIG. 2 when the balloon is inflated.

FIG. 3 illustrates the balloon catheter 20 when the balloon is in an expanded state/configuration. As illustrated in FIG. 3, the mechanical waveguide 26 is secured to the external face of the balloon 24 at a connection point 32. When the balloon 24 is inflated, the mechanical waveguide 26 follows the lateral motion of the balloon 24 so that the distance d between the mechanical waveguide 26 and the catheter shaft 22 increases.

It should be understood for the person skilled in the art that the balloon may have similar construction and operation as existing balloon medical devices in that it may comprise a so-called single lumen or double-lumen construction and that it may be of the so-called compliant, super-compliant, semi-compliant or non-compliant type as known in the art.

In one embodiment, the location of the connection point 32 on the surface of the balloon 24 is chosen as a function of a desired orientation for the mechanical waveguide 26 relative to the catheter shaft 22 or a desired position and/or orientation of the distal end of the mechanical waveguide 26 with respect to the distal end 30 of the catheter shaft 22, when the balloon 24 is inflated. For example, if the connection point 32 is chosen to be located on the section of the balloon 24 that is adjacent to the distal end 30 of the catheter, then the distal end of the mechanical waveguide 26 will be oriented towards the longitudinal axis along which the catheter shaft 22 extends when the balloon 24 is inflated. In another example, if the connection point 32 is chosen to be located on the section of the balloon 24 that is opposite to the distal end 30 of the catheter, then the distal end of the mechanical waveguide 26 will be oriented away from the longitudinal axis when the balloon 24 is inflated.

It should be understood that any adequate device, apparatus or system for inflating the balloon 24 may be used. For example, a mechanical device such as pump may be used for inflating the balloon 24. In another example, a fluid delivery system may be used for inflating the balloon 24. The fluid delivery system comprises a source of fluid which is fluidly connected to the balloon 24. The source of fluid is adapted to inject fluid such as air or water into the balloon 24 in order to inflate the balloon 24 and aspirate the fluid from the balloon 24 in order to deflate the balloon 24.

In one embodiment, the mechanical waveguide 26 is fixedly secured to the balloon 24. In another embodiment, the mechanical waveguide 26 is movably secured to the balloon 24. For example, the mechanical waveguide 26 may be movable relative to the balloon 24 along the longitudinal axis along which the catheter shaft 22 extends while having a fixed position relative to the balloon 24 along an axis orthogonal to the surface of the balloon 24. For example, at least one ring may be secured to the external face of the balloon 24 at different locations along the length of the balloon 24 and the mechanical waveguide 26 may be inserted into the rings and slide along the length of the balloon 24. In another example, a tubular structure such as a sheath may be secured to the external face of the balloon 24 along at least a portion of the length of the balloon 24 and the mechanical waveguide 26 may be inserted into the sheath and slide within the sheath so as to be longitudinally moveable relative to the balloon 24.

While in the embodiment illustrated in FIGS. 2 and 3 the mechanical waveguide 26 is secured to the balloon 24 at a single connection point 32, it should be understood that other configurations are possible. For example, the mechanical waveguide 26 may be secured to the balloon 24 at several discrete connection points along the length of the balloon 24. In another example, at least a section of the mechanical waveguide 26 may be continuously secured to at least a section of the balloon 24.

In one embodiment, the mechanical waveguide 26 is further fixedly or movably secured to the section of the catheter shaft 22 which is not covered by the balloon 24.

While in the illustrated embodiment the mechanical waveguide 26 is secured to the balloon 24 so as to be parallel to the catheter shaft 22, it should be understood that other configurations are possible. For example, the mechanical waveguide 26 may be wrapped around the balloon 24 in a helicoidal manner. In this case, it should be understood that the mechanical waveguide 26 is moveably secured to the balloon 24 so as to follow the expansion of the balloon 26.

In one embodiment, the balloon comprises a single external expendable wall such as wall 24. In this case, the fluid used to inflate the balloon 24 is comprised between the internal face of the external wall and the catheter shaft 22. In another embodiment, the balloon may comprise an external wall and an internal wall which are secured together at a distal end of the balloon. The internal wall may have tubular shape defining an aperture in which the catheter shaft 22 is inserted and the internal is fixedly secured to the catheter shaft. At the proximal end of the balloon, a tube for injecting and/or aspirating a fluid between the internal and external walls of the balloon may be inserted between the internal and external walls which are hermetically secured together and/or around the tube.

While the distal end of the mechanical waveguide 26 has a linear shape, it should be understood that other configurations may be possible. For example, the distal end of the mechanical waveguide 26 may be inwardly curved towards the longitudinal axis or outwardly curved away from the longitudinal axis. The extremity of the distal end of the mechanical waveguide 26 may take on various shapes. For example the extremity may be rounded, square, beveled, or an inclined plane relative to the axis of the distal tip. Other geometries may also be possible.

It should be understood that the position of the distal end of the mechanical waveguide 26 relative to the distal end 30 of the catheter when the balloon 24 is inflated may vary. In the illustrated embodiment, the distal end of the mechanical waveguide 26 when the balloon 24 is inflated is substantially coplanar with the distal end 30 of the catheter shaft 22. In another embodiment, the distal end of the mechanical waveguide 26 when the balloon 24 is inflated may project from the distal end 30 of the catheter shaft 22 in a forward direction away from the distal end 30 of the catheter shaft 22. In a further embodiment, the distal end of the mechanical waveguide 26 when the balloon 24 is inflated is located between the proximal and distal ends 28 and 30 of the catheter shaft 22.

While the mechanical waveguide 26 is secured to the outer surface of the balloon 24, the person skilled in the art would understand that the mechanical waveguide 26 may be inserted into the balloon 24. In this case, the mechanical waveguide 26 may be secured to the internal face of the balloon 24.

Figure 4B:
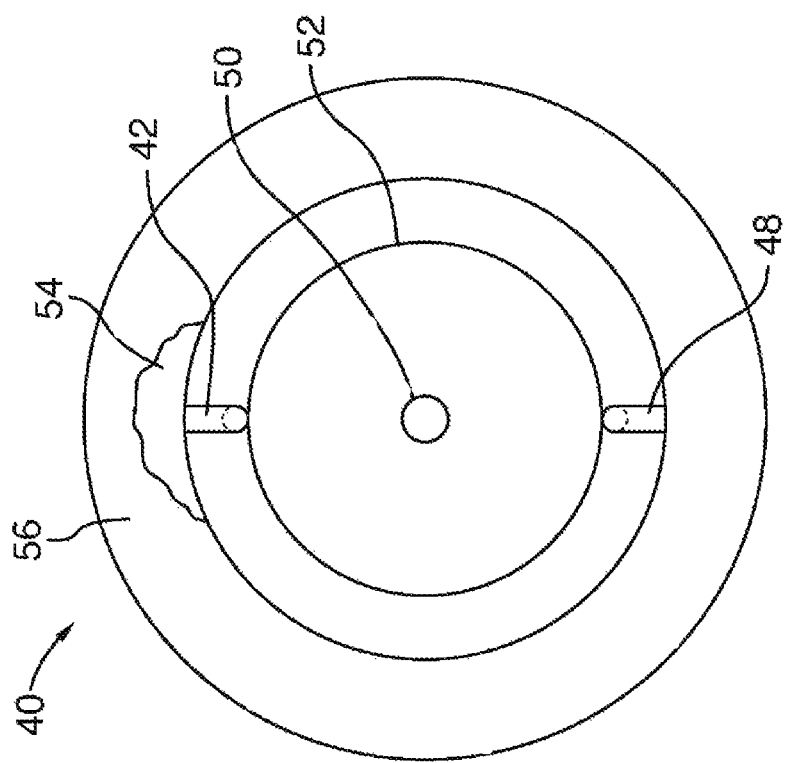
FIG. 4B is a front view of the catheter of FIG. 4A when inserted into a blood vessel, in accordance with an embodiment.
Figure 4A:
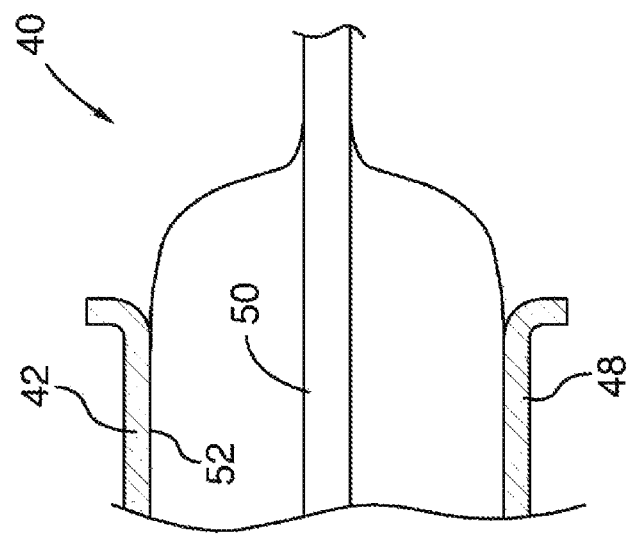
FIG. 4A is a cross-sectional view of a catheter balloon comprising four mechanical waveguides secured outside of a balloon, in accordance with an embodiment.

While the balloon catheter 20 comprises a single mechanical waveguide 26, FIGS. 4A and 4B illustrate a balloon catheter 40 which comprises two mechanical waveguides 42 and 48. The balloon catheter 40 further comprises a catheter shaft 50 and a balloon 52 which is secured to the catheter shaft 50. It should be understood that the number of mechanical waveguides 42 and 48 is exemplary only.

A guide wire is inserted into the catheter shaft 50 and used for guiding the balloon 52 to the target lesion 54 to be treated. The balloon catheter 40 is inserted into a blood vessel 56 of a patient until the balloon 52 be adjacent to the lesion 54. The mechanical waveguides 42 and 48 are arranged around the balloon 52 to obtain a desired energy deposition pattern at the lesion to be treated which either surrounds the balloon 52 or is at the distal tip of the balloon 52. In the illustrated embodiment, the mechanical waveguides 42 and 48 are secured to the external face of the balloon 52 and evenly distributed around the circumference of the balloon 52 when inflated. The distal end of the mechanical waveguides 42 and 48 is outwardly curved away from the catheter shaft 50 to allow treatment of lesions located around the balloon 52.

Once the balloon catheter 40 has been inserted into the blood vessel 54 so that the balloon 52 be at an adequate position relative to the lesion 54 to be treated, the balloon 52 is inflated. During the inflation of the balloon 52, the radial position of the mechanical waveguides 42 and 48 moves outwardly until at least one of the mechanical waveguides 42 and 48 reaches the inner surface of the blood vessel 56 to be treated or be at a desired location relative to the lesion 54 to be treated. Once the mechanical waveguides have been adequately positioned, mechanical waves such as shock waves or ultrasound pulses are generated and propagated along at least one of the mechanical waveguides 42 and 48 in order to treat the lesion 54.

While the mechanical waveguides 42 and 48 extend linearly along a longitudinal axis which corresponds to the longitudinal axis of the catheter shaft 50, it should be understood that other configurations may be possible. For example, the mechanical waveguides 42 and 48 may be circumferentially arranged along the balloon periphery or they may be arranged in a helicoidal arrangement around the balloon periphery. Similarly, while the distal end of the mechanical waveguides 42 and 48 is outwardly curved, other configurations are possible. For example, the distal end of some of the mechanical waveguides 42 and 48 may straight to treat lesions located in front of the balloon 52 while the distal end of other mechanical waveguides 42 and 48 may be outwardly curved to treat lesions located around the circumference of the balloon 52.

While the distal end of the mechanical waveguides 42 and 48 is substantially coplanar with the distal end of the catheter shaft 50, it should be understood that the distal end of the mechanical waveguides 42 and 48 relative to that of the catheter shaft 50 may vary. For example, the distal end of some of the mechanical waveguides 42 and 48 may project from the distal end of the catheter shaft 50 to treat lesions located in front of the catheter shaft 50 while the distal end of other mechanical waveguides 42 and 48 may be located between the proximal and distal ends of the catheter shaft 50 to treat lesions located around the circumference of the balloon 52.

In one embodiment, the location at which the treatment is performed and/or the energy deposition pattern at the lesion is adjusted by adequately choosing the shape of the balloon 52 and adequately inflating the balloon 52, i.e., controlling the inflation of the balloon 52 such as by controlling the pressure of the fluid injected into the balloon 52. The balloon 52 may be inflated gradually as the treatment progresses, thereby allowing the mechanical waveguides to successively treat different lesion areas at an increasing diameter.

Figure 5:
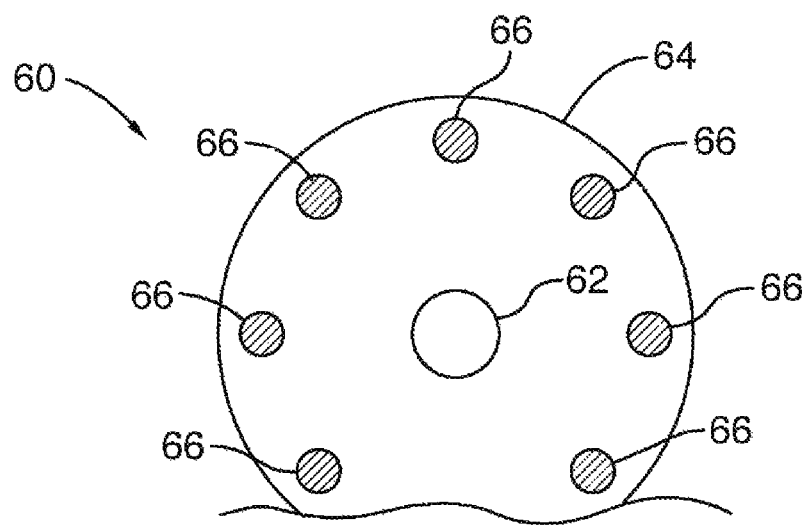
FIG. 5 schematically illustrates a balloon catheter in which mechanical waveguides are evenly distributed about the circumference of a balloon, in accordance with an embodiment.
Figure 6:
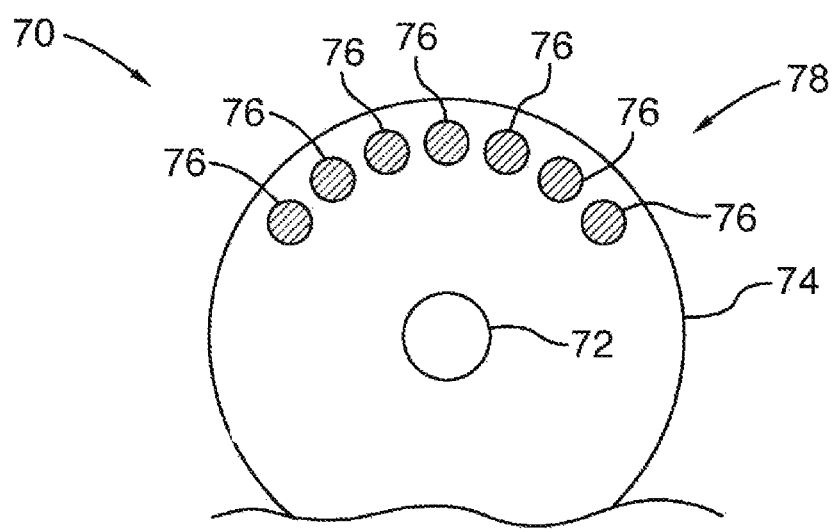
FIG. 6 schematically illustrates a balloon catheter in which mechanical waveguides are concentrated at single area along the circumference of a balloon, in accordance with an embodiment.

While FIGS. 4A and 4B illustrates a balloon catheter 40 in which the mechanical waveguides 42 and 48 are positioned on the outer surface of the balloon 52, FIGS. 5 and 6 illustrates embodiments of a balloon catheter in which mechanical waveguides are inserted into a balloon.

FIG. 5 illustrates a balloon catheter 60 that comprises a catheter shaft 62, an inflatable balloon 64 secured to the catheter shaft 62 and mechanical waveguides 66 which are inserted into the balloon 64. The mechanical waveguides 66 are evenly and symmetrically distributed around the internal circumference of the balloon 64.

While the mechanical waveguides 66 are evenly and symmetrically distributed around the internal circumference of the balloon 64, other configurations may be possible. For example, FIG. 6 illustrates a balloon catheter 70 that comprises a catheter shaft 72, an inflatable balloon 74 secured to the catheter shaft 72 and seven mechanical waveguides 76 which are asymmetrically inserted into the balloon 74. The mechanical waveguides 76 are concentrated on a given area 78 of the internal circumference of the balloon 74. In another example, mechanical waveguides may be arranged asymmetrically and/or concentrated at different locations around the circumference of the balloon.

In an embodiment in which mechanical waveguides are inserted into a balloon, the distal end of the mechanical waveguides may extend outside of the balloon. In another embodiment, the distal end of the mechanical waveguides may be located within the balloon. In this case, the distal end of the mechanical waveguides may be in contact with the internal face of the balloon and the balloon may be fabricated with a material that permits good acoustic coupling between the waveguide and the tissue outside the balloon. In a further embodiment, some of the mechanical waveguides may extend outside of the balloon while the distal end of other mechanical waveguides may be located within the balloon.

It should be understood that the number, position, shape, and dimensions of the mechanical waveguides may be chosen as a function of a desired energy deposition pattern of the balloon catheter device.

In an embodiment in which they are arranged on the outside face of the balloon, the mechanical waveguides may be covered by an external sheath. In this case, the distal end of the mechanical waveguides may be located inside the sheath or may protrude outside the sheath. If it remains inside the sheath, the distal end of the mechanical waveguides may be in physical contact with the inside surface of the sheath and the sheath may be fabricated with a material that permits good acoustic coupling between the waveguide and the tissue outside the sheath.

In one embodiment, the mechanical waveguides may be individually enclosed in a tube whether the mechanical waveguides are located inside or outside of a balloon. The tubes may be made of acoustically-insulating material to minimize mechanical energy loss before the distal end of the waveguides.

In an embodiment in which mechanical waveguides are located on the outer surface of a balloon, the mechanical waveguides may be arranged according to more than one row or layer when the balloon is deflated and arranged according to a single row or layer when the balloon is inflated.

Figure 7:
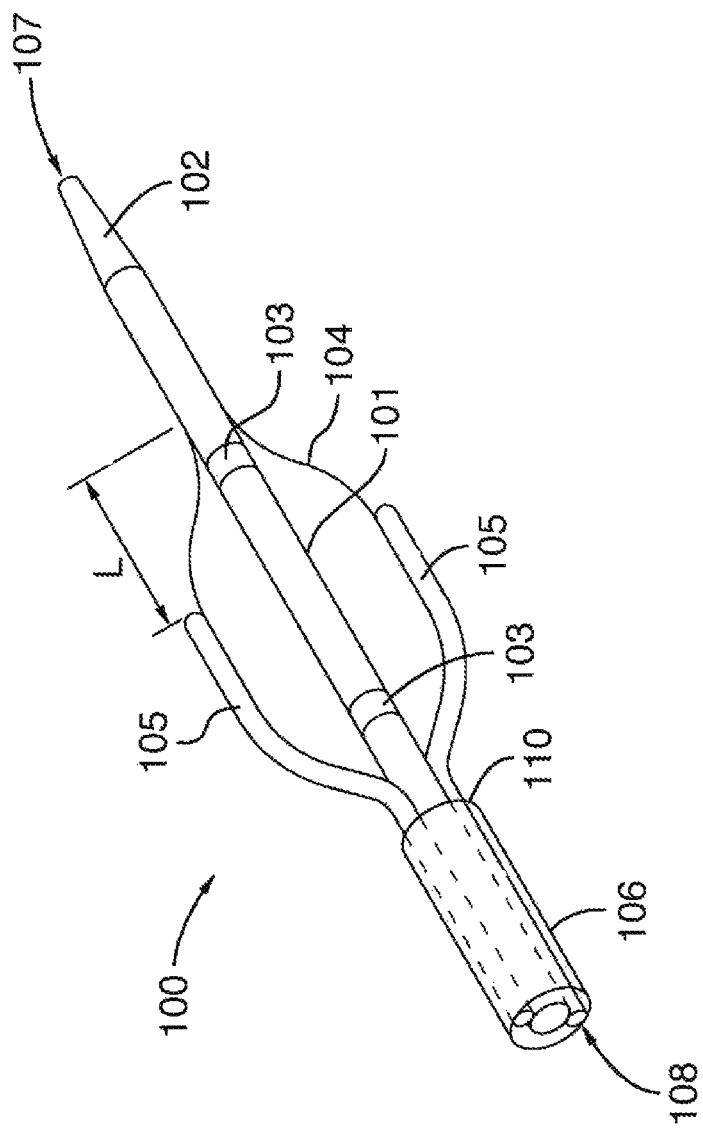
FIG. 7 is a perspective view of a balloon catheter device comprising a catheter shaft, a transparent balloon secured to the catheter and two mechanical waveguides secured to the external face of the transparent balloon, in accordance with an embodiment.
Figure 8:
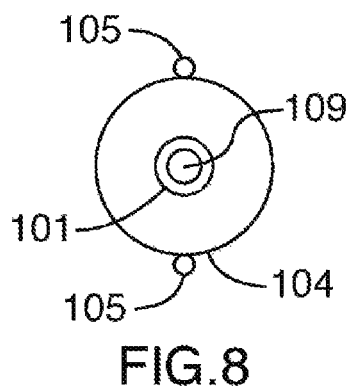
FIG. 8 is a cross-section view of the balloon catheter device of FIG. 7.

FIGS. 7 and 8 illustrate a balloon catheter 100 which comprises two mechanical waveguides 105 secured on the outer surface of the balloon 104 on opposite sides thereof. The balloon catheter 100 further comprises a catheter shaft 101 which extends between a proximal end 108 of the catheter balloon 100 and a distal end 107 of the catheter balloon 100. The catheter shaft 101 comprises a distal tip portion 102 adjacent to the distal end 107 of the balloon catheter 100 and the diameter of the distal tip portion 102 decreases towards the distal end 107 of the catheter balloon 100. The catheter shaft 101 is provided with two radiopaque markers 103 which are each secured to the external face of the catheter shaft 101 each a respective position along the length thereof in order to indicate the extent of the length of the balloon 104. The catheter shaft 101 is provided with a central lumen 109 which extends between its proximal and distal ends for insertion of a guidewire therein. At the proximal end 108 of the balloon catheter 100, the mechanical waveguides are arranged around the catheter shaft 101 and covered by a sheath 106 which terminates at its distal portion 110 before the proximal end of the balloon 104. The proximal end (not shown) of the mechanical waveguides is operatively connected to a mechanical pulse generator. The portion of the mechanical waveguides 105 secured to the balloon 104 follows the external surface of the balloon 104 and moves according to the expansion/compression of the balloon 104. The distal tip 111 of the mechanical waveguides terminates at a distance "L" from the distal end of the balloon 104.

In some embodiments, the balloon may comprise a double wall and the mechanical waveguides are inserted between or within the two walls of the balloon.

Figure 9:
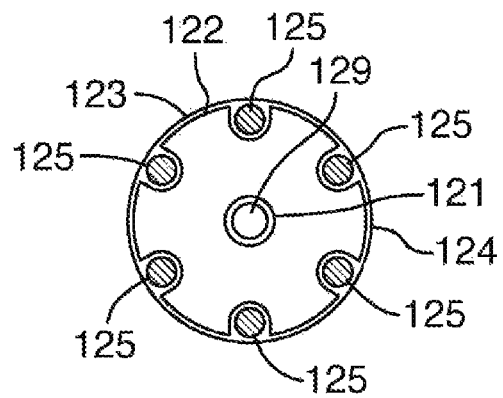
FIG. 9 is a transversal cross-sectional view of a balloon catheter device comprising a catheter shaft, a balloon secured to the catheter and having an external wall and an internal wall defining six recesses, and six mechanical waveguides each inserted into a respective recess, in accordance with an embodiment.
Figure 10:
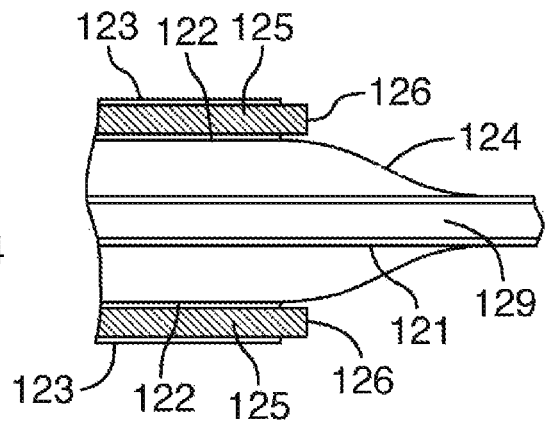
FIG. 10 is a partial longitudinal cross-sectional view of the balloon catheter device of FIG. 9.

FIGS. 9 and 10 illustrate a balloon catheter which comprises a catheter shaft 121 having a tubular shape and extending between a proximal end and a distal end. The catheter shaft 121 is provided with a central aperture or lumen 129 which extends between the proximal and distal ends of the catheter shaft 121. An inflatable balloon 124 is secured around the catheter shaft 121. The balloon 124 comprises an external wall 123 and an internal wall 122 positioned within the external wall 123. The proximal ends of the internal and external walls 122 and 123 are hermetically secured together around the catheter shaft 121 and the distal ends of the internal and external walls 122 and 123 are hermetically secured together around the catheter shaft 121.

The balloon catheter further comprises six mechanical waveguides 125 which are inserted between the internal and external walls 122 and 123. The external wall 123 has a circular cross-sectional shape while the internal wall 122 defines six inwardly extending recesses each shaped and sized for receiving a respective mechanical waveguide 125. Each recess extends along a given longitudinal section of the balloon 124. The sections of the internal wall 122 located between two adjacent recesses are secured to the external wall 123. For each recess, the external wall 123 comprises a proximal aperture and a distal aperture each aligned with a respective recess for insertion of a respective mechanical waveguide 125. Each recess and its respective proximal and distal apertures in the external wall 123 form a hole which extends through the given section of the balloon 124. Each mechanical waveguide 125 is inserted in a respective hole and the distal end of each mechanical waveguide 124 projects forwardly from the distal end of the hole as illustrated in FIG. 10.

In one embodiment, the mechanical waveguides 125 are fixedly secured within their respective hole in the balloon 124 so that each mechanical waveguide 125 has a fixed position relative to the balloon 124. In another embodiment, the mechanical waveguides 125 are movably inserted into their respective hole through the balloon so that the position of the distal end of the mechanical waveguides 125 may be varied relative to the distal end of the catheter shaft 121.

It should be understood that the external wall 123 may comprise no distal apertures so that the distal end of each mechanical waveguide 125 is located within its respective hole. Alternatively, not all of the recesses are provided with a respective distal aperture in the external wall 123 so that the distal end of only some of the mechanical waveguides 125 may extend forwardly from the balloon 124.

It should be understood that a fluid is inserted into the cavity formed between the internal wall 122 and the catheter shaft 121 in order to inflate/deflate the balloon 124. By controlling the pressure of the fluid within the cavity, the expansion and size of the balloon may be controlled, thereby controlling the position of the distal end of the mechanical waveguides 125 relative to the catheter shaft 121.

Figure 11:
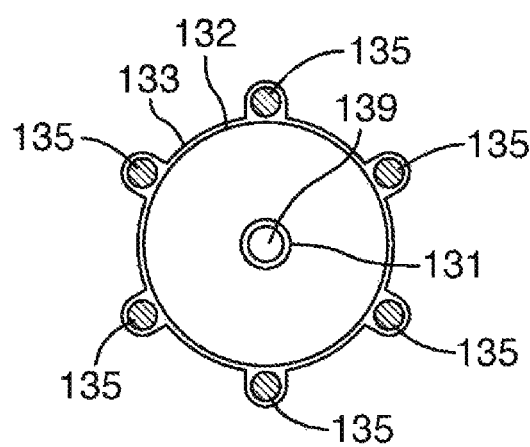
FIG. 11 is a transversal cross-sectional view of a balloon catheter device comprising a catheter shaft, a balloon secured to the catheter and having an external wall defining six protrusions and an internal wall, and six mechanical waveguides each inserted into a respective recess, in accordance with an embodiment.
Figure 12:
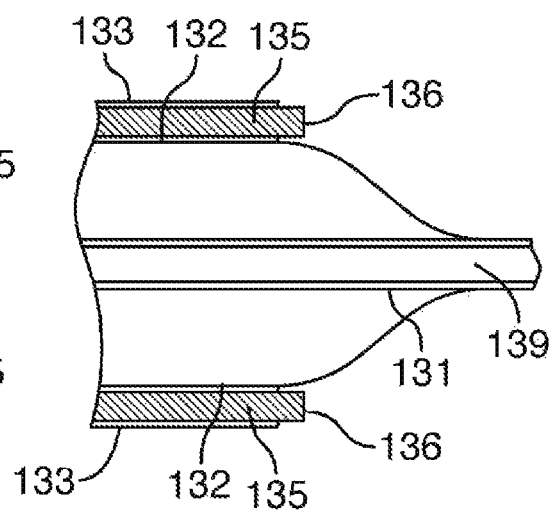
FIG. 12 is a partial longitudinal cross-sectional view of the balloon catheter device of FIG. 11.

It should be understood that the number of mechanical waveguides 125 may vary as long as the balloon catheter comprises at least one mechanical waveguide 125. Similarly, the number of holes within the balloon 124 may also vary accordingly. The position on the balloon 124, shape and/or the length of the holes within the balloon 124 may also vary FIGS. 11 and 12 illustrate an embodiment of a balloon catheter which comprises a catheter shaft 131 having a tubular shape and extending between a proximal end and a distal end. The catheter shaft 131 is provided with a central aperture or lumen 139 which extends between the proximal and distal ends of the catheter shaft 131. An inflatable balloon 134 is secured around the catheter shaft 131. The balloon 134 comprises an external wall 133 and an internal wall 132 positioned within the external wall 133. In an embodiment in which the internal and external walls 132 and 133 are substantially the same length, the proximal ends of the internal and external walls 132 and 133 are hermetically secured together around the catheter shaft 131 and the distal ends of the internal and external walls 132 and 133 are also hermetically secured together around the catheter shaft 131. Alternatively, the external wall 133 may be shorter than the internal wall 132 and the distal and proximal ends of the external may be secured to the external face of the internal wall 132 while only the proximal and distal ends of the internal wall 132 are hermetically secured to the catheter shaft 131.

The balloon catheter further comprises six mechanical waveguides 135 which are inserted between the internal and external walls 132 and 133. The internal wall 133 has a circular cross-sectional shape while the external wall 133 defines six outwardly extending protrusions each shaped and sized for receiving a respective mechanical waveguide 135. Each protrusion extends along a given longitudinal section of the balloon 134. The sections of the external wall 133 located between two adjacent protrusions are secured to the internal wall 132. For each protrusion, the external wall 133 comprises a proximal aperture and a distal aperture each aligned with a respective protrusion for insertion of a respective mechanical waveguide 135. Each protrusion and its respective proximal and distal apertures in the external wall 133 form a hole which extends through the given section of the balloon 134. Each mechanical waveguide 135 is inserted in a respective hole and the distal end of each mechanical waveguide 134 projects forwardly from the distal end of the hole as illustrated in FIG. 12.

In one embodiment, the mechanical waveguides 135 are fixedly secured within their respective hole in the balloon 134 so that each mechanical waveguide 135 has a fixed position relative to the balloon 134. In another embodiment, the mechanical waveguides 135 are movably inserted into their respective hole through the balloon so that the position of the distal end of the mechanical waveguides 135 may be varied relative to the distal end of the catheter shaft 131.

It should be understood that the external wall 133 may comprise no distal apertures so that the distal end of each mechanical waveguide 135 is located within its respective hole within the balloon 134. Alternatively, not all of the recesses may be provided with a respective distal aperture in the external wall 133 so that the distal end of only some of the mechanical waveguides 135 may extend forwardly from the balloon 134.

It should be understood that a fluid is inserted into the cavity formed between the internal wall 132 and the catheter shaft 131 in order to inflate/deflate the balloon 134. By controlling the pressure of the fluid within the cavity, the expansion and size of the balloon 134 may be controlled, thereby controlling the position of the distal end of the mechanical waveguides 135 relative to the catheter shaft 131.

Figure 13:
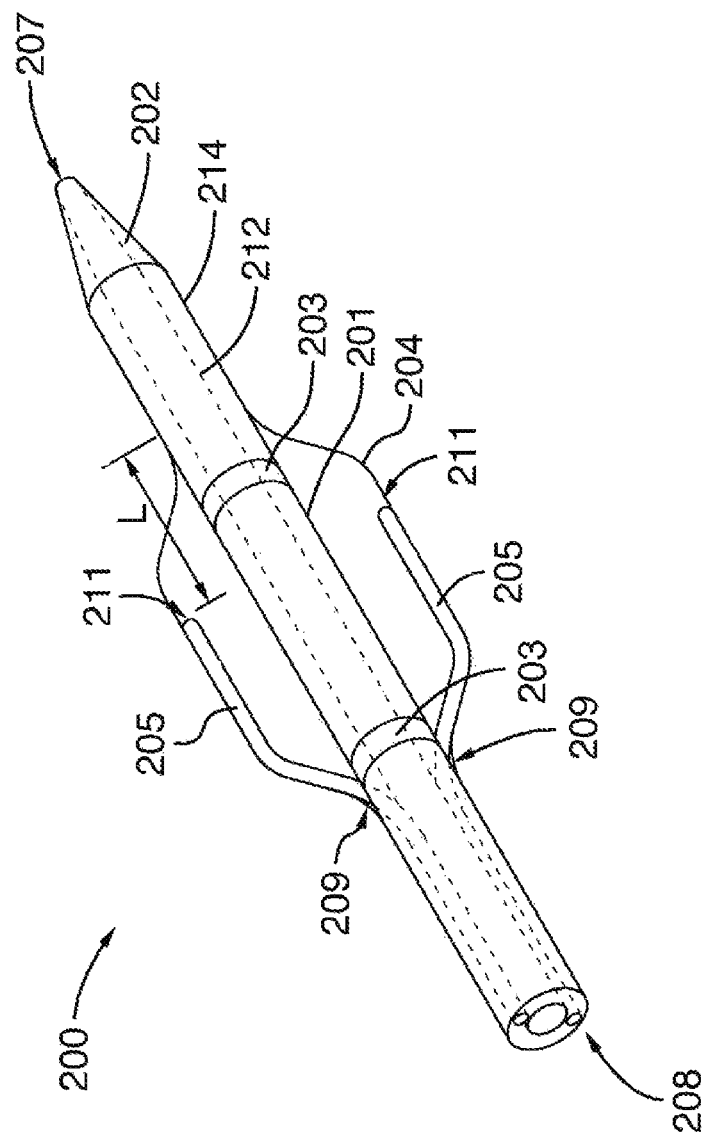
FIG. 13 is a perspective view of a balloon catheter device comprising a catheter shaft, a transparent balloon secured to the catheter and two mechanical waveguides inserted into the transparent balloon and having a section secured to the internal face of the balloon, in accordance with an embodiment.

It should be understood that the number of mechanical waveguides 135 may vary as long as the balloon catheter comprises at least one mechanical waveguide 135. Similarly, the number of holes within the balloon 134 may also vary accordingly. The position on the balloon 134, shape and/or the length of the holes within the balloon 134 may also vary FIG. 13 illustrates one embodiment of a balloon catheter 200 which comprises a catheter shaft 201, a balloon 204 and two mechanical waveguides 205. The catheter shaft 201 extends between a proximal end 208 and a distal end 207 and comprises an internal wall 212 and an external wall 214 having each a tubular shape. The external wall 214 comprises a central aperture in which the internal wall 212 is inserted while being fixedly secured to the external wall 214. The distal end of the external wall 214 is secured to the internal wall 212. The two mechanical waveguides 205 are inserted within the aperture of the external wall 214 between the internal face of the external wall 214 and the external face of the internal wall 212. The internal wall 212 also defines an aperture that extends between the proximal and distal ends of the catheter shaft 201. In one embodiment, the internal wall 212 is provided with an end wall at the distal end thereof so that the aperture defined by the internal wall 212 does not extend through the distal end thereof. In another embodiment, no end wall is provided at the distal end of the internal wall 212 so that the aperture extends through the distal end of the internal wall 212.

The external wall 214 is provided with two apertures each sized and shaped for receiving a respective mechanical 205 therethrough and allowing the mechanical waveguides 205 to be inserted from the space defined between the internal and external walls 212 and 214 into the cavity present between the balloon 204 and the external wall 214 of the catheter shaft 201. In the illustrated embodiment, the two apertures through the external wall 214 are located at a position 209 adjacent to the proximal end of the balloon 204 and the portion of each mechanical waveguide 205 that is inserted into the balloon 204 is in physical contact with the internal face of the balloon 204. Each mechanical waveguide 204 is inserted into the balloon 204 so that its distal end be located at a given distance L from the distal end of the balloon 204.

In one embodiment, the distal end of the mechanical waveguides 205 has a fixed position relative to the distal end of the balloon 204 so that the distance L may not vary. In this case, the distal end of the mechanical waveguides 205 may be fixedly secured to the internal face of the balloon 204. In another embodiment, the distal end of the mechanical waveguides 205 has a movable position relative to the distal end of the balloon 204 so that the distance L may vary. In this case and for each mechanical waveguide 205, the balloon 204 may be provided with rings or a sheath secured to its internal face and in which the mechanical waveguide is slidably inserted so that the mechanical waveguide 205 may slide along the internal face of the balloon 204 and the distal end of the mechanical waveguide 205 may be positioned at an adequate distance L from the distal end of the balloon 204.

In one embodiment, each mechanical waveguide 205 is sealingly inserted into its respective aperture through the external wall 214 so that no fluid present in the balloon 204 may flow into the space defined between the internal and external walls 212 and 214 via the aperture in which the mechanical waveguide is inserted. For example, a sealing gasket may be inserted in the aperture between the mechanical waveguide 205 and the external wall 214. In one embodiment, the sealing gasket allows a motion of the mechanical waveguide 205 relative to the external wall 214.

In another embodiment, fluid may flow from the balloon 204 into the space defined between the internal and external walls 212 and 214 via the aperture in which the mechanical waveguide is inserted. For example, the size of the apertures may be greater than that of the mechanical waveguides 205.

In one embodiment, the space defined between the internal and external walls 212 and 214 of the catheter shaft 201 and the mechanical waveguides 205 is used for injecting fluid into the balloon 204 from the proximal end of the catheter shaft 201. In one embodiment, the mechanical waveguides may not be sealingly secured to the external wall 214 so that the fluid may flow into the balloon 204 via the apertures of the external wall 214 in which the mechanical waveguides 205 are inserted. In another embodiment, the mechanical waveguides 205 may be sealingly inserted into their respective aperture through the external wall 214. In this case, the external wall 214 is provided with at least one further aperture through which the fluid may enter and exit the balloon 204. The fluid may be directly injected into the space defined between the internal and external walls 212 and 214 of the catheter shaft 201 and the mechanical waveguides 205. Alternatively, a tube connected to a fluid delivery system at a proximal end thereof may be inserted into the space defined between the internal and external walls 212 and 214 of the catheter shaft 201 and the mechanical waveguides 205 and the distal end of the tube is fluidly connected to the interior of the balloon 204 via the further aperture. In this embodiment, the distal end of the aperture of the internal wall 212 may be open to allow the use of a guide wire.

In another embodiment, the aperture of the internal wall 212 is used for injecting fluid into the balloon 204 and/or aspirating fluid from the balloon 204. In this case, the distal end of the aperture of the internal wall 212 is sealingly closed. The internal wall 212 comprises a first connecting hole and the external wall 214 comprises a second connection hole. A connection tube has a first end sealingly secured to the first connection hole of the internal wall 212 and a second end sealingly secured to the second connection hole of the external wall 214 so as to fluidly connect the aperture of the internal wall 212 to the internal space of the balloon. The proximal end of the aperture of the internal wall 212 is fluidly connected to a fluid delivery system so as to inject fluid into the balloon 204 and/or aspirate fluid from the balloon 204. In one embodiment, each mechanical waveguide 205 is sealingly inserted into its respective aperture through the external wall 214 so that no fluid may flow from the balloon 204 into the space defined between the internal and external walls 212 and 214 of the catheter shaft 201 and the mechanical waveguides 205.

In one embodiment, the catheter shaft 201 is further provided with two radiopaque markers 203 on the internal face of the external wall 214. The radiopaque markers are positioned so to each be located within the balloon 204 and adjacent to a respective end of the balloon 204. The radiopaque markers 203 act as reference markers to visualize the position of the ends of the balloon 204 and/or indicate the extent of the length of the balloon 204.

It should be understood that the diameter of the aperture present in the external wall 214 is chosen to be at least equal to the addition of the external diameter of the internal wall 212 and the diameter of the mechanical waveguide 205. In the illustrated embodiment, the diameter the aperture present in the external wall 214 is at least equal to the external diameter of the internal wall 212 plus twice the diameter of the mechanical waveguide 209.

In one embodiment, a distal tip portion 202 of the catheter shaft 201 is located adjacent to the distal end 207 thereof. Within the distal tip portion 202, the diameter of the external wall 214 reduces towards the distal end 207 of the catheter shaft 201 so that the internal diameter of the external wall 214 be equal to the external diameter of the internal wall at the distal end 207 of the catheter shaft 201.

Figure 14:
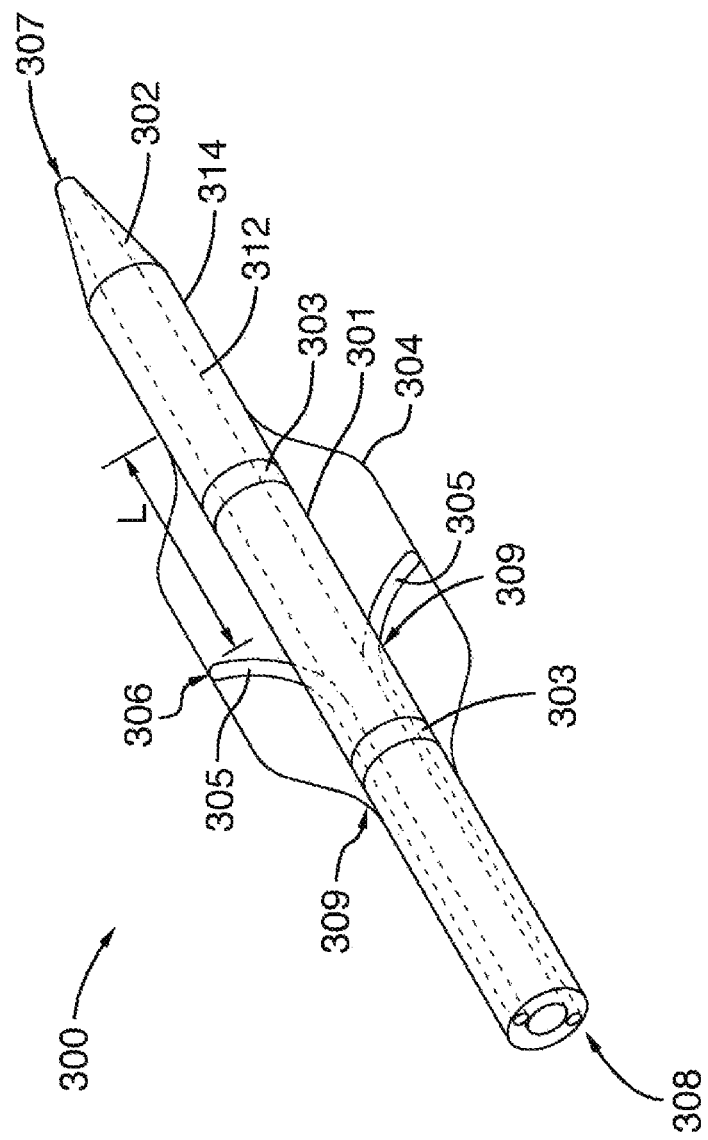
FIG. 14 is a perspective view of a balloon catheter device comprising a catheter shaft, a transparent balloon secured to the catheter and two mechanical waveguides inserted into the transparent balloon and having a distal end abutting against the internal face of the balloon, in accordance with an embodiment.

FIG. 14 illustrates one embodiment of a balloon catheter 300 which comprises a catheter shaft 301, a balloon 304 and two mechanical waveguides 305. The catheter shaft 301 extends between a proximal end 308 and a distal end 307 and comprises an internal wall 312 and an external wall 314 having each a tubular shape. The external wall 314 comprises a central aperture in which the internal wall 312 is inserted while being fixedly secured to the external wall 314. The distal end of the external wall 314 is secured to the internal wall 312. The two mechanical waveguides 305 are inserted within the aperture of the external wall 314 between the internal face of the external wall 314 and the external face of the internal wall 312. The internal wall 312 also defines an aperture that extends between the proximal and distal ends of the catheter shaft 301. In one embodiment, the internal wall 312 is provided with an end wall at the distal end thereof so that the aperture defined by the internal wall 312 does not extend through the distal end thereof. In another embodiment, no end wall is provided at the distal end of the internal wall 312 so that the aperture extends through the distal end of the internal wall 312.

The external wall 314 is provided with two apertures each sized and shaped for receiving a respective mechanical 305 therethrough and allowing the mechanical waveguides 305 to be inserted from the space defined between the internal and external walls 312 and 314 into the cavity present between the balloon 304 and the external wall 314 of the catheter shaft 301. In the illustrated embodiment, the two apertures through the external wall 314 are located at a position 309 which is away from the proximal end of the balloon 304 and the mechanical waveguides 305 each emerge outwardly from their respective aperture towards the wall of the balloon 304. The mechanical waveguides 305 are positioned within the balloon 304 so that their distal end abuts against the internal face of the balloon 304 at a connection point 306 and located at a given distance L from the distal end of the balloon 304.

In one embodiment, the distal end of the mechanical waveguides 305 has a fixed position relative to the distal end of the balloon 304 so that the distance L may not vary. In this case, the distal end of the mechanical waveguides 305 may be fixedly secured to the internal face of the balloon 304. In another embodiment, the distal end of the mechanical waveguides 305 has a movable position relative to the distal end of the balloon 304 so that the distance L may vary. In this case, the curvature of the section of the mechanical waveguides inserted into the balloon 304 may be changed so as to change the position of the contact points between the distal end of the mechanical waveguides 305 and the internal face of the balloon 304.

In one embodiment, each mechanical waveguide 305 is sealingly inserted into its respective aperture through the external wall 314 so that no fluid present in the balloon 304 may flow into the space defined between the internal and external walls 312 and 314 via the aperture in which the mechanical waveguide 305 is inserted. For example, a sealing gasket may be inserted in the aperture between the mechanical waveguide 305 and the external wall 314. In one embodiment, the sealing gasket allows a motion of the mechanical waveguide 305 relative to the external wall 314.

In another embodiment, fluid may flow from the balloon 304 into the space defined between the internal and external walls 312 and 314 via the aperture in which the mechanical waveguide is inserted. For example, the size of the apertures may be greater than that of the mechanical waveguides 305.

In one embodiment, the space defined between the internal and external walls 312 and 314 of the catheter shaft 301 and the mechanical waveguides 305 is used for injecting fluid into the balloon 304 from the proximal end of the catheter shaft 301. In one embodiment, the mechanical waveguides may not be sealingly secured to the external wall 314 so that the fluid may flow into the balloon 304 via the apertures of the external wall 314 in which the mechanical waveguides 305 are inserted. In another embodiment, the mechanical waveguides 305 may be sealingly inserted into their respective aperture through the external wall 314. In this case, the external wall 314 is provided with at least one further aperture through which the fluid may enter and exit the balloon 304. The fluid may be directly injected into the space defined between the internal and external walls 312 and 314 of the catheter shaft 301 and the mechanical waveguides 305. Alternatively, a tube connected to a fluid delivery system at a proximal end thereof may be inserted into the space defined between the internal and external walls 312 and 314 of the catheter shaft 301 and the mechanical waveguides 305 and the distal end of the tube is fluidly connected to the interior of the balloon 304 via the further aperture. In this embodiment, the distal end of the aperture of the internal wall 312 may be open to allow the use of a guide wire.

In another embodiment, the aperture of the internal wall 312 is used for injecting fluid into the balloon 304 and/or aspirating fluid from the balloon 304. In this case, the distal end of the aperture of the internal wall 312 is sealingly closed. The internal wall 312 comprises a first connecting hole and the external wall 314 comprises a second connection hole. A connection tube has a first end sealingly secured to the first connection hole of the internal wall 312 and a second end sealingly secured to the second connection hole of the external wall 314 so as to fluidly connect the aperture of the internal wall 312 to the internal space of the balloon. The proximal end of the aperture of the internal wall 312 is fluidly connected to a fluid delivery system so as to inject fluid into the balloon 304 and/or aspirate fluid from the balloon 304. In one embodiment, each mechanical waveguide 305 is sealingly inserted into its respective aperture through the external wall 314 so that no fluid may flow from the balloon 304 into the space defined between the internal and external walls 312 and 314 of the catheter shaft 301 and the mechanical waveguides 305.

In one embodiment, the catheter shaft 301 is further provided with two radiopaque markers 303 on the internal face of the external wall 314. The radiopaque markers are positioned so to each be located within the balloon 304 and adjacent to a respective end of the balloon 304. The radiopaque markers 303 act as reference markers to visualize the position of the ends of the balloon 304 and/or indicate the extent of the length of the balloon 304.

It should be understood that the diameter of the aperture present in the external wall 314 is chosen to be at least equal to the addition of the external diameter of the internal wall 312 and the diameter of the mechanical waveguide 309. In the illustrated embodiment, the diameter the aperture present in the external wall 314 is at least equal to the external diameter of the internal wall 312 plus twice the diameter of the mechanical waveguide 309.

In one embodiment, a distal tip portion 302 of the catheter shaft 301 is located adjacent to the distal end 307 thereof. Within the distal tip portion 302, the diameter of the external wall 314 reduces towards the distal end 307 of the catheter shaft 301 so that the internal diameter of the external wall 314 be equal to the external diameter of the internal wall at the distal end 307 of the catheter shaft 301.

Figure 15:
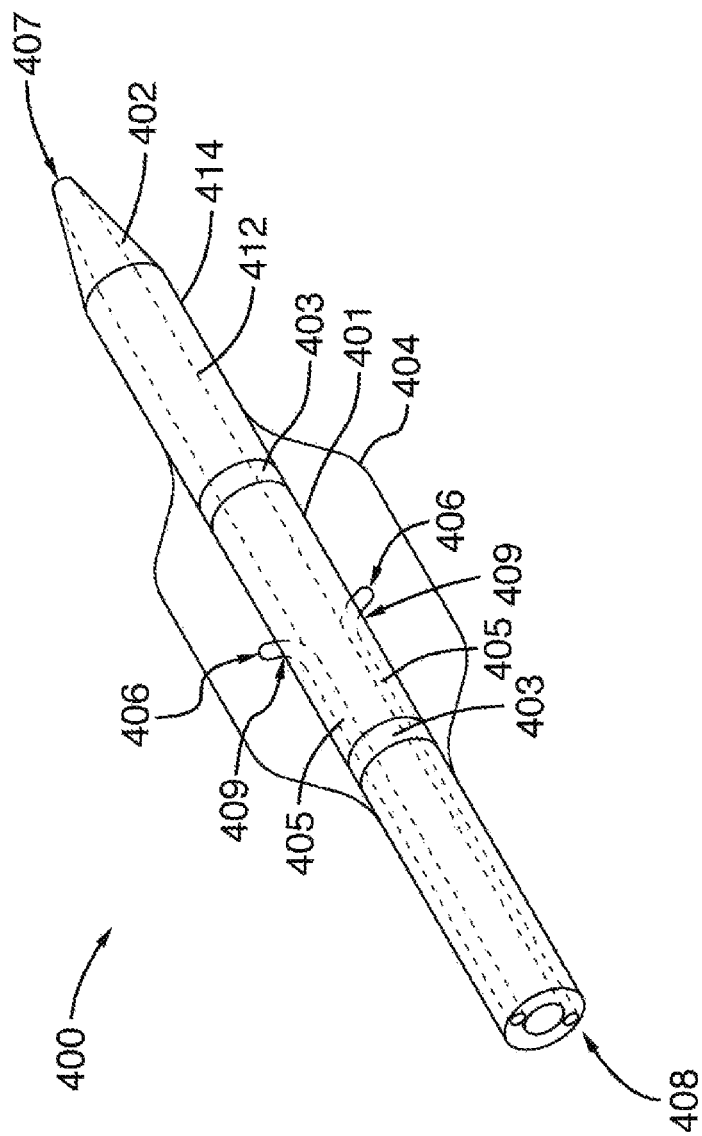
FIG. 15 is a perspective view of a balloon catheter device comprising a catheter shaft, a transparent balloon secured to the catheter and two mechanical waveguides inserted into the transparent balloon and having a free distal end located within the balloon, in accordance with an embodiment.

FIG. 15 illustrates one embodiment of a balloon catheter 400 which comprises a catheter shaft 401, a balloon 404 and two mechanical waveguides 405. The catheter shaft 401 extends between a proximal end 408 and a distal end 407 and comprises an internal wall 412 and an external wall 414 having each a tubular shape. The external wall 414 comprises a central aperture in which the internal wall 412 is inserted while being fixedly secured to the external wall 414. The distal end of the external wall 414 is secured to the internal wall 412. The two mechanical waveguides 405 are inserted within the aperture of the external wall 414 between the internal face of the external wall 414 and the external face of the internal wall 412. The internal wall 412 also defines an aperture that extends between the proximal and distal ends of the catheter shaft 401. In one embodiment, the internal wall 412 is provided with an end wall at the distal end thereof so that the aperture defined by the internal wall 412 does not extend through the distal end thereof. In another embodiment, no end wall is provided at the distal end of the internal wall 412 so that the aperture extends through the distal end of the internal wall 412.

The external wall 414 is provided with two apertures each sized and shaped for receiving a respective mechanical 405 therethrough and allowing the mechanical waveguides 405 to be inserted from the space defined between the internal and external walls 412 and 414 into the cavity present between the balloon 404 and the external wall 414 of the catheter shaft 401. In the illustrated embodiment, the two apertures through the external wall 414 are each located at a position 409 which is away from the proximal end of the balloon 404 and the mechanical waveguides 405 each emerge outwardly from their respective aperture towards the wall of the balloon 404. The section of the mechanical waveguide 405 adjacent to the distal end 406 thereof is curved. The mechanical waveguides 405 are positioned within the balloon 404 so that their distal end 406 be free within the balloon 404.

In one embodiment, the distal end of the mechanical waveguides 405 has a fixed position relative to the distal end of the balloon 404. In this case, the distal end of the mechanical waveguides 405 may be fixedly secured to the internal face of the balloon 404. In another embodiment, the distal end of the mechanical waveguides 405 has a movable position within the balloon 404.

In one embodiment, each mechanical waveguide 405 is sealingly inserted into its respective aperture through the external wall 414 so that no fluid present in the balloon 404 may flow into the space defined between the internal and external walls 412 and 414 via the aperture in which the mechanical waveguide 405 is inserted. For example, a sealing gasket may be inserted in the aperture between the mechanical waveguide 405 and the external wall 414. In one embodiment, the sealing gasket allows a motion of the mechanical waveguide 405 relative to the external wall 414.

In another embodiment, fluid may flow from the balloon 404 into the space defined between the internal and external walls 412 and 414 via the aperture in which the mechanical waveguide is inserted. For example, the size of the apertures in the external wall 414 may be greater than that of the mechanical waveguides 405.

In one embodiment, the space defined between the internal and external walls 412 and 414 of the catheter shaft 401 and the mechanical waveguides 405 is used for injecting fluid into the balloon 404 from the proximal end of the catheter shaft 401. In one embodiment, the mechanical waveguides may not be sealingly secured to the external wall 414 so that the fluid may flow into the balloon 404 via the apertures of the external wall 414 in which the mechanical waveguides 405 are inserted. In another embodiment, the mechanical waveguides 405 may be sealingly inserted into their respective aperture through the external wall 414. In this case, the external wall 414 is provided with at least one further aperture through which the fluid may enter and exit the balloon 404. The fluid may be directly injected into the space defined between the internal and external walls 412 and 414 of the catheter shaft 401 and the mechanical waveguides 405. Alternatively, a tube connected to a fluid delivery system at a proximal end thereof may be inserted into the space defined between the internal and external walls 412 and 414 of the catheter shaft 401 and the mechanical waveguides 405 and the distal end of the tube is fluidly connected to the interior of the balloon 404 via the further aperture. In this embodiment, the distal end of the aperture of the internal wall 412 may be open to allow the use of a guide wire.

In another embodiment, the longitudinal aperture of the internal wall 412 is used for injecting fluid into the balloon 404 and/or aspirating fluid from the balloon 404. In this case, the distal end of the longitudinal aperture of the internal wall 412 is sealingly closed. The internal wall 412 comprises a first connecting hole and the external wall 414 comprises a second connection hole. A connection tube has a first end sealingly secured to the first connection hole of the internal wall 412 and a second end sealingly secured to the second connection hole of the external wall 414 so as to fluidly connect the aperture of the internal wall 412 to the internal space of the balloon. The proximal end of the aperture of the internal wall 412 is fluidly connected to a fluid delivery system so as to inject fluid into the balloon 404 and/or aspirate fluid from the balloon 404. In one embodiment, each mechanical waveguide 405 is sealingly inserted into its respective aperture through the external wall 414 so that no fluid may flow from the balloon 404 into the space defined between the internal and external walls 412 and 414 of the catheter shaft 401 and the mechanical waveguides 405.

In one embodiment, the catheter shaft 401 is further provided with two radiopaque markers 403 on the internal face of the external wall 414. The radiopaque markers are positioned so to each be located within the balloon 404 and adjacent to a respective end of the balloon 404. The radiopaque markers 403 act as reference markers to visualize the position of the ends of the balloon 404 and/or indicate the extent of the length of the balloon 404.

It should be understood that the diameter of the aperture present in the external wall 414 is chosen to be at least equal to the addition of the external diameter of the internal wall 412 and the diameter of the mechanical waveguide 409. In the illustrated embodiment, the diameter the aperture present in the external wall 414 is at least equal to the external diameter of the internal wall 412 plus twice the diameter of the mechanical waveguide 409.

In one embodiment, a distal tip portion 402 of the catheter shaft 401 is located adjacent to the distal end 407 thereof. Within the distal tip portion 402, the diameter of the external wall 414 reduces towards the distal end 407 of the catheter shaft 401 so that the internal diameter of the external wall 414 be equal to the external diameter of the internal wall at the distal end 407 of the catheter shaft 401.

Figure 21:
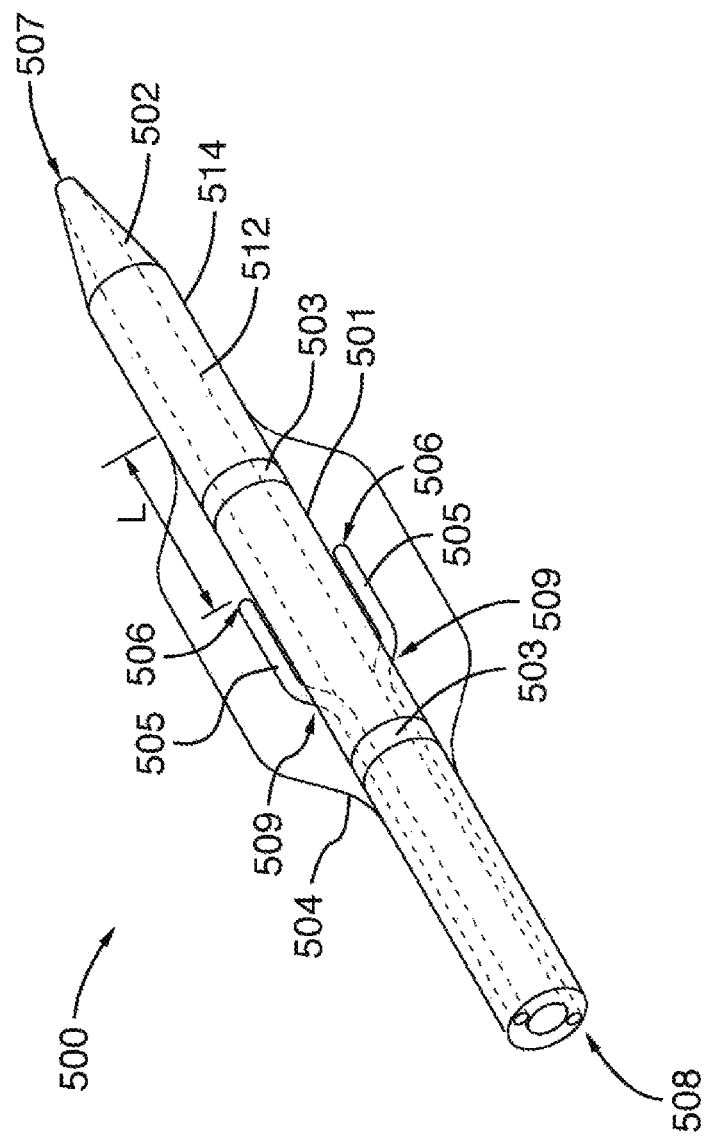
FIG. 21 is a perspective view of a balloon catheter device comprising a catheter shaft, a transparent balloon secured to the catheter and two mechanical waveguides inserted into the transparent balloon and having a section secured to the external face of the catheter shaft, in accordance with an embodiment.

FIG. 21 illustrates one embodiment of a balloon catheter 500 which comprises a catheter shaft 501, a balloon 504 and two mechanical waveguides 505. The catheter shaft 501 extends between a proximal end 508 and a distal end 507 and comprises an internal wall 512 and an external wall 514 having each a tubular shape. The external wall 514 comprises a central aperture in which the internal wall 512 is inserted while being fixedly secured to the external wall 514. The distal end of the external wall 514 is secured to the internal wall 512. The two mechanical waveguides 505 are inserted within the aperture of the external wall 514 between the internal face of the external wall 514 and the external face of the internal wall 512. The internal wall 512 also defines an aperture that extends between the proximal and distal ends of the catheter shaft 501. In one embodiment, the internal wall 512 is provided with an end wall at the distal end thereof so that the aperture defined by the internal wall 512 does not extend through the distal end thereof. In another embodiment, no end wall is provided at the distal end of the internal wall 512 so that the aperture extends through the distal end of the internal wall 512.

The external wall 514 is provided with two apertures each sized and shaped for receiving a respective mechanical 505 therethrough and allowing the mechanical waveguides 505 to be inserted from the space defined between the internal and external walls 512 and 514 into the cavity present between the balloon 504 and the external wall 514 of the catheter shaft 501. In the illustrated embodiment, the two apertures through the external wall 514 are located at a position 509 which is away from the proximal end of the balloon 504 and the mechanical waveguides 505 each emerge outwardly from their respective aperture towards the wall of the balloon 504. The mechanical waveguides 505 are positioned within the balloon 504 so that a distal section of the mechanical waveguide 505 adjacent to the distal end 506 thereof extends along and adjacent to the external face of the external wall 514 of the catheter shaft 501. In one embodiment the distal section of the mechanical waveguides may be secured to the external wall 514 of the catheter shaft 501.

In one embodiment, the distal end of the mechanical waveguides 505 has a fixed position relative to the distal end of the balloon 504 so that the distance L between the distal end 506 of the mechanical waveguide 505 and the distal end of the balloon 504 may not vary. In this case, the distal end of the mechanical waveguides 505 may be fixedly secured to the external face of the external wall 514. In another embodiment, the distal end 506 of the mechanical waveguides 505 has a movable position relative to the distal end of the balloon 504 so that the distance L may vary. In this case, rings or a sheath may be secured to the In one embodiment, each mechanical waveguide 505 is sealingly inserted into its respective aperture through the external wall 514 so that no fluid present in the balloon 504 may flow into the space defined between the internal and external walls 512 and 514 via the aperture in which the mechanical waveguide 505 is inserted. For example, a sealing gasket may be inserted in the aperture between the mechanical waveguide 505 and the external wall 514. In one embodiment, the sealing gasket allows a motion of the mechanical waveguide 505 relative to the external wall 514.

In another embodiment, fluid may flow from the balloon 504 into the space defined between the internal and external walls 512 and 514 via the aperture in which the mechanical waveguide is inserted. For example, the size of the apertures may be greater than that of the mechanical waveguides 505.

In one embodiment, the space defined between the internal and external walls 512 and 514 of the catheter shaft 501 and the mechanical waveguides 505 is used for injecting fluid into the balloon 504 from the proximal end of the catheter shaft 501. In one embodiment, the mechanical waveguides may not be sealingly secured to the external wall 514 so that the fluid may flow into the balloon 504 via the apertures of the external wall 514 in which the mechanical waveguides 505 are inserted. In another embodiment, the mechanical waveguides 505 may be sealingly inserted into their respective aperture through the external wall 514. In this case, the external wall 514 is provided with at least one further aperture through which the fluid may enter and exit the balloon 504. The fluid may be directly injected into the space defined between the internal and external walls 512 and 514 of the catheter shaft 501 and the mechanical waveguides 505. Alternatively, a tube connected to a fluid delivery system at a proximal end thereof may be inserted into the space defined between the internal and external walls 512 and 514 of the catheter shaft 501 and the mechanical waveguides 505 and the distal end of the tube is fluidly connected to the interior of the balloon 504 via the further aperture. In this embodiment, the distal end of the aperture of the internal wall 512 may be open to allow the use of a guide wire.

In another embodiment, the aperture of the internal wall 512 is used for injecting fluid into the balloon 504 and/or aspirating fluid from the balloon 504. In this case, the distal end of the aperture of the internal wall 512 is sealingly closed. The internal wall 512 comprises a first connecting hole and the external wall 514 comprises a second connection hole. A connection tube has a first end sealingly secured to the first connection hole of the internal wall 512 and a second end sealingly secured to the second connection hole of the external wall 514 so as to fluidly connect the aperture of the internal wall 512 to the internal space of the balloon. The proximal end of the aperture of the internal wall 512 is fluidly connected to a fluid delivery system so as to inject fluid into the balloon 504 and/or aspirate fluid from the balloon 504. In one embodiment, each mechanical waveguide 505 is sealingly inserted into its respective aperture through the external wall 514 so that no fluid may flow from the balloon 504 into the space defined between the internal and external walls 512 and 514 of the catheter shaft 501 and the mechanical waveguides 505.

In one embodiment, the catheter shaft 501 is further provided with two radiopaque markers 503 on the internal face of the external wall 514. The radiopaque markers are positioned so to each be located within the balloon 504 and adjacent to a respective end of the balloon 504. The radiopaque markers 503 act as reference markers to visualize the position of the ends of the balloon 504 and/or indicate the extent of the length of the balloon 504.

It should be understood that the diameter of the aperture present in the external wall 514 is chosen to be at least equal to the addition of the external diameter of the internal wall 512 and the diameter of the mechanical waveguide 509. In the illustrated embodiment, the diameter the aperture present in the external wall 514 is at least equal to the external diameter of the internal wall 512 plus twice the diameter of the mechanical waveguide 509.

In one embodiment, a distal tip portion 502 of the catheter shaft 501 is located adjacent to the distal end 507 thereof. Within the distal tip portion 502, the diameter of the external wall 514 reduces towards the distal end 507 of the catheter shaft 501 so that the internal diameter of the external wall 514 be equal to the external diameter of the internal wall at the distal end 507 of the catheter shaft 501.

It should be understood that the distal end of the mechanical waveguides 205, 305, 405 and 505 is operatively connected to source of mechanical waves and/or pulses.

Figure 16:
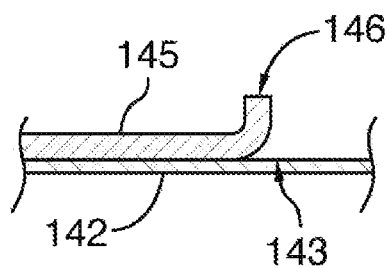
FIG. 16 illustrates a mechanical waveguide secured to the external face of a balloon and having a curved distal end, in accordance with an embodiment.
Figure 17:
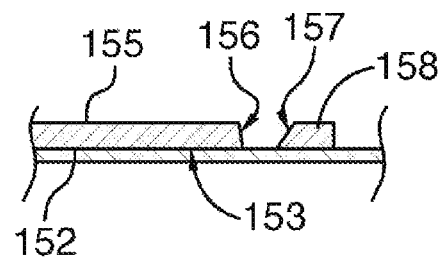
FIG. 17 illustrates a mechanical waveguide and a deflector both secured to the external face of a balloon, in accordance with an embodiment.

FIGS. 16 and 17 illustrate various tip geometries for mechanical waveguides arranged on the outside surface of a balloon catheter used to deflect and/or orient the mechanical waves emitted by the mechanical waveguides. The embodiments shown in FIGS. 16 and 17 may be used in conjunction with the embodiments shown in FIGS. 11 and 12.

FIG. 16 illustrates mechanical waveguide 145 arranged on the outside surface 143 of a balloon. The distal tip 146 of the mechanical waveguide 145 is curved outwards. It should be understood that the curvature of the tip 146 of the mechanical waveguide 145 may be chosen as a function of a desired energy deposition pattern.

FIG. 17 illustrates one embodiment of a balloon catheter which comprises a deflection device to deflect, reflect and/or orient the mechanical waves emitted by a mechanical waveguide. A mechanical waveguide 155 is secured to the outer face 153 of a balloon 152 and a deflector 158 is also secured to the outer face of the balloon so as to face the distal end 156 of the mechanical waveguide 155 in order to deflect, reflect and/or orient the mechanical waves emitted by the mechanical waveguide 155 according to a desired orientation. It should be understood that any adequate device adapted to deflect or reflect mechanical waves may be used. In one embodiment, the deflector 158 is adjustable so that the deflection or reflection orientation and/or distance between the distal tip 156 of a mechanical waveguide 155 and the proximal end 157 of the deflection device 158 may be adjusted to correspond to a desired direction to propagate the mechanical waves propagating from the distal end 156 of the mechanical waveguide 155 in a desired direction. For example, the distal end 156 of the mechanical waveguide 155 may be positioned to emit mechanical waves in the direction of the longitudinal axis of the catheter and the deflector 158 may redirect the mechanical waves in the radial direction, i.e., in a direction substantially orthogonal to the longitudinal axis. In one embodiment, the deflector 158 may be covered by a sheath made with an acoustic coupling material. It should be understood that the number, position, shape, and dimensions of the deflectors may be chosen as a function of a desired energy deposition pattern of the balloon catheter device.

Figure 18:
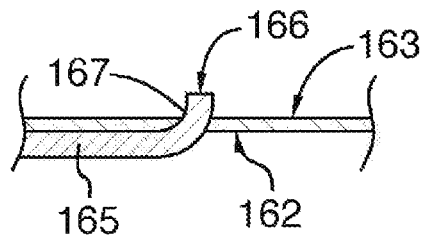
FIG. 18 illustrates a mechanical waveguide secured to the internal face of a balloon and having a curved distal end that projects outside of the balloon, in accordance with an embodiment.
Figure 19:
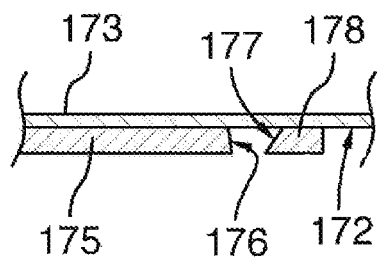
FIG. 19 illustrates a mechanical waveguide and a deflector both secured to the internal face of a balloon, in accordance with an embodiment.
Figure 20:
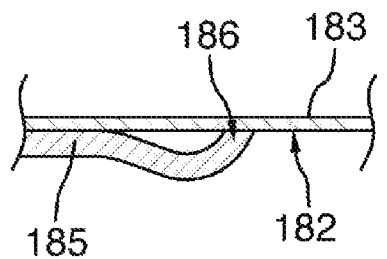
FIG. 20 illustrates a mechanical waveguide secured to the internal face of a balloon and having a curved distal end abutting against the internal face of the balloon, in accordance with an embodiment.

FIGS. 18, 19 and 20 illustrate various mechanical waveguide tip geometries for mechanical waveguides arranged on the inside surface of a balloon used to deflect and/or orient the mechanical waves emitted by the mechanical waveguides. The embodiments shown in FIGS. 18, 19 and 20 may be used in conjunction with the embodiments shown in FIGS. 9 and 10.

FIG. 18 shows a mechanical waveguide 165 arranged on the inside surface 162 of a balloon. The balloon is provided with a hole through which the outwardly curved distal tip 166 of the mechanical waveguide 165 is sealingly inserted. In one embodiment, the distal tip 166 of the mechanical waveguide 165 emerges flush with the outer surface 163 of the mechanical waveguide 165. In another embodiment the distal tip 166 of the mechanical waveguide 165 emerges beyond the outer surface 163 the balloon.

FIG. 19 illustrates one embodiment of a balloon catheter which comprises a deflection device to deflect, reflect and/or orient the mechanical waves emitted by the mechanical waveguides. The balloon catheter comprises a balloon 173 and a mechanical waveguide 175 which is located on the inner face 172 of the balloon 173. The balloon catheter further comprises a deflector 178 which is positioned so as to face the distal end 176 of the mechanical waveguide 175 in order to deflect, reflect and/or orient the mechanical waves emitted by the mechanical waveguide 175 according to a desired orientation. It should be understood that any adequate device adapted to deflect or reflect mechanical waves may be used. In one embodiment, the deflector 178 is adjustable so that the deflection or reflection orientation and/or distance between the distal tip 176 of a mechanical waveguide 175 and the proximal end 177 of the deflection device 178 may be adjusted to correspond to a desired direction to propagate the mechanical waves propagating from the distal end of the mechanical waveguide in the desired direction. For example, the distal end 176 of the mechanical waveguide 175 may be positioned to emit mechanical waves in the direction of the longitudinal axis of the catheter and the deflector 178 may redirect the mechanical waves in the radial direction, i.e., in a direction substantially orthogonal to the longitudinal axis. It should be understood that the number, position, shape, and dimensions of the deflectors may be chosen as a function of a desired energy deposition pattern of the balloon catheter device.

FIG. 20 shows a mechanical waveguide 185 arranged on the inner surface 182 of a balloon 183. The section of the mechanical waveguide 185 adjacent to the distal tip 186 is curved outwardly so that the distal tip 186 abuts against the inner surface 182 the balloon 183.

In one embodiment, the outer surface of the balloon or the sheath, if any, may be coated with a drug (or similar) that can diffuse into the surrounding tissue before, during or after the mechanical wave emission from the mechanical waveguide(s). In one embodiment, the mechanical wave emission from the mechanical waveguides may promote more efficient drug uptake from the surrounding tissue.

In one embodiment, the balloon catheter may comprise a double-wall balloon and the space between the two walls of the balloon may contain a drug (or the like). Delivery of the drug may be triggered from the proximal end of the balloon catheter device with a mechanism running along the length of the device. Delivery of the drug may also be triggered by the emission of mechanical waves at the distal end of the balloon catheter.

In one embodiment, the balloon catheter device further comprises one or more fluid (i.e., liquid and/or gas) delivery tubes to deliver fluids containing drugs, vaccines or other therapeutic substances to the lesion to be treated. In the same of another embodiment, the delivery tubes may be used to deliver fluids to cool/heat the lesion to be treated, for example. This fluid delivery can be performed before, concurrently or after mechanical energy exposure. In a further embodiment, the tubes may be used for aspirating debris caused by the treatment.

In one embodiment, the balloon catheter may comprise a drug (or similar) capsule at the distal end thereof that can be triggered (liberated) from its proximal end with a mechanism running along the length of the device.

In one embodiment, a drug (or similar) capsule may be located at the distal end of the balloon catheter and the capsule can be triggered (liberated) by the emission of mechanical waves at the distal end of the balloon catheter.

In one embodiment, the balloon catheter further comprises an optical coherence tomography (OCT) or intravascular ultrasound (IVUS) imaging device between the inner catheter and the outside surface of the balloon.

In one embodiment, the balloon catheter may be covered with a hydrophilic, hydrophobic or friction reducing coating, or a combination thereof.

In one embodiment, the above-described balloon catheter and method may be used to treat both calcified and fibrotic lesions while minimizing arterial wall tissue injury and emboli size.

It should be understood that the balloon may have any adequate shape. For example, the shape of the inflated balloon may be essentially a circular cylinder.

The embodiments of the invention described above are intended to be exemplary only. The scope of the invention is therefore intended to be limited solely by the scope of the appended claims.

We claim:

1. A device for delivering high amplitude and broadband mechanical pulses to treat a lesion present in a blood vessel, comprising:
    a catheter body extending between a first proximal end and a first distal end along a longitudinal axis;
    an inflatable balloon secured to the catheter body and being adjustable between an inflated configuration and a deflated configuration, the inflatable balloon being fluidly connectable to a source of fluid for varying a configuration of the balloon; and
    at least one mechanical waveguide extending between a second proximal end operatively connectable to a source of high amplitude and broadband mechanical pulses and a second distal end for propagating the high amplitude and broadband mechanical pulses from the second proximal end to the second distal end, the mechanical waveguide being secured to at least a portion of the catheter body between the first proximal end and the first distal end thereof.

2. The device of claim 1, wherein the at least one mechanical waveguide is secured to one of an internal face and an external face of the inflatable balloon.

3. The device of claim 2, wherein the second distal end of the at least one mechanical waveguide is coplanar with the first distal end of the catheter body when the inflatable balloon is inflated.

4. The device of claim 2, wherein the second distal end of the at least one mechanical waveguide projects from the first distal end of the catheter body when the inflatable balloon is inflated.

5. The device of claim 2, wherein the second distal end of the at least one mechanical waveguide is located between the proximal and distal ends of the catheter body when the inflatable balloon is inflated.

6. The device of claim 2, wherein the at least one mechanical waveguide is movably secured to the one of the internal face and the external face of the inflatable balloon.

7. The device of claim 2, further comprising at least one deflector facing the second distal end of a respective one of the at least one mechanical waveguide, and wherein the at least one deflector is adapted to deflect the mechanical pulses radially.

8. The device of claim 1, wherein at least a section of the at least one mechanical waveguide is inserted inside the inflatable balloon.

9. The device of claim 8, wherein the inflatable balloon comprises an internal wall facing the catheter body and an external wall comprising at least one aperture on a distal face thereof, the at least one mechanical waveguide extending at least partially between the internal and external walls each through a respective one of the at least one aperture.

10. The device of claim 9, wherein the internal wall has a substantially circular cross-section shape and the external wall defines at least one protrusion each receiving a respective one of the at least one mechanical waveguide.

11. The device of claim 9, wherein the external wall has a substantially circular cross-section shape and the internal wall defines at least one recess each receiving a respective one of the at least one mechanical waveguide.

12. The device of claim 8, wherein the catheter body comprises an internal wall and an external wall spaced apart from the internal wall, the at least one mechanical waveguide being inserted between the internal and external walls, the external wall comprising at least one aperture and the at least one mechanical waveguide being inserted into a respective one of the at least one aperture so as to partially extend within the inflatable balloon.

13. The device of claim 12, wherein the at least one mechanical waveguide is sealingly inserted into the respective one of the at least one aperture.

14. The device of claim 12, wherein the second distal end of the at least one mechanical waveguide is positioned within the inflatable balloon.

15. The device of claim 14, further comprising at least one deflector facing the second distal end of a respective one of the at least one mechanical waveguide.

16. The device of claim 12, wherein the inflatable balloon comprises at least one hole and the second distal end of the at least one mechanical waveguide is sealingly inserted into a respective one of the at least one hole.

17. The device of claim 16, wherein the second distal end of the at least one mechanical waveguide projects outside of the inflatable balloon.

18. The device of claim 1, wherein the at least one mechanical waveguide comprises a plurality of mechanical waveguides.

19. The device of claim 18, wherein the mechanical waveguides are arranged according to at least two rows when the inflatable balloon is in the deflated configuration and according a single row when the inflatable balloon is in the inflated configuration.

20. The device of claim 1, further comprising at least one waveguide tube in which a respective one of the at least one mechanical waveguide is inserted.

21. The device of claim 1, wherein an external face of the inflatable balloon is coated with one of: a drug, a hydrophilic coating, a hydrophobic coating and a friction reducing coating.

22. The device of claim 1, further comprising at least one optical fiber for delivery of laser energy.

23. The device of claim 1, wherein a distal tip at the second distal end of the at least one mechanical waveguide is not secured to the catheter body and the inflatable balloon.

* * * * *